United States Patent [19]
Silva et al.

[11] Patent Number: 5,494,440
[45] Date of Patent: Feb. 27, 1996

[54] DENTAL ARTICULATOR

[75] Inventors: Robert Silva; Patti J. Silva, both of Lakewood, Colo.

[73] Assignee: Condylator, Inc., Lakewood, Colo.

[21] Appl. No.: 245,618

[22] Filed: May 19, 1994

[51] Int. Cl.⁶ .......................... A61C 11/00; A61C 19/00
[52] U.S. Cl. .................. 433/58; 433/57; 433/59
[58] Field of Search .................. 433/54, 57, 58, 433/59, 64

[56] References Cited

U.S. PATENT DOCUMENTS

| | | | |
|---|---|---|---|
| 1,338,918 | 5/1920 | Hall | 433/58 |
| 2,043,394 | 6/1936 | Reith | 433/58 X |
| 2,556,639 | 6/1951 | Wimberly | 433/58 |
| 4,175,325 | 11/1979 | Beckwith | 433/58 X |
| 4,764,113 | 8/1988 | Hiranuma | 433/58 X |
| 5,366,373 | 11/1994 | Mumolo et al. | 433/58 |

OTHER PUBLICATIONS

1978, *Fundamentals of Fixed Posthodontics*, Herbert T. Shillingburg, Jr., Sumiya Hobo, Lowell D. Whitsett, pp. 55–58, 224–228.

1993, Zahn Dental Company, Inc., catalog, pp. 43–46.

Apr, 1994 LMT, Lab Management Today, pp. 29–36.

*Primary Examiner*—Nicholas D. Lucchesi
*Attorney, Agent, or Firm*—Holland & Hart

[57] ABSTRACT

A dental articulator includes an upper frame member and a lower frame member modeled substantially after a maxilla and mandible of a human jaw, respectively. The upper frame member includes a mounting area for attachment of an upper or maxillary dental cast. Two opposing fossae on the upper frame member include downwardly opening sockets similar to the fossae of a human jaw. The lower frame member includes a mounting area for attachment of a lower or mandibular dental cast. Two opposing condyles extend upwardly from the lower frame member to fit within the sockets of the fossae on the upper frame member. An elastic band is placed around the upper and lower frame members to yieldingly maintain the condyles within the sockets of the fossae. Each condyle/fossa pair forms a temporomandibular joint similar to that in a human jaw and allows the lower frame member to undergo protrusive and excursive movements which closely simulate the movement of a human mandible.

15 Claims, 3 Drawing Sheets

DENTAL ARTICULATOR

FIELD OF THE INVENTION

The present invention relates to dental articulators used in the fabrication of dental restorations, and more particularly to dental articulators which closely model the complex motion of the human jaw.

BACKGROUND OF THE INVENTION

Dental articulators are mechanical devices which are used during the fabrication of dental restorations to simulate the movement of the human jaw. The human jaw comprises essentially an upper jaw or "maxilla" and a lower jaw or "mandible" together with accompanying muscles and ligaments. Movement of the human jaw is accomplished by movement of the mandible relative to the maxilla. The connection of the mandible to the maxilla is made by two opposing (left and right) ball and socket type joints at the posterior of the jaw. The maxilla includes the two opposing fossae defining downturned sockets, while the mandible includes two enlarged bone portions or "balls" known as condyles. The ball and socket connection between each human fossa and condyle is referred to as a temporomandibular joint.

Movement of the human mandible results from two types of movement within the temporomandibular joint: rotational movement about different axes through the condyles and translational movement of the condyles themselves. A protrusive movement, where the mandible slides forward to align the upper and lower (maxillary and mandibular) teeth, is an example of a primarily translational movement of the condyles within the temporomandibular joint. The rotational movement of the mandible can occur about three different axes. First, the mandible may rotate about a horizontal or "hinge" axis which passes through the two separate condyles within the opposing temporomandibular joints. Second, during a lateral excursion in which the mandible moves toward one side (the working side), there is rotational movement of the mandible about a vertical axis which passes through the condyle on the working side (i.e., for a left lateral excursion, the mandible rotates about a vertical axis passing through the left condyle). Third, during a lateral excursion, the non-working condyle tends to drop down or move in a downward arc so that the condyle on the working side rotates about a second horizontal or "sagittal" axis perpendicular to both the hinge axis and the vertical axis (i.e., for a left lateral excursion, the mandible rotates about a sagittal axis passing through the left condyle).

The range of movement of a patient's mandible is determined by, among other things, the temporomandibular joints of the patient's jaw and the guiding contact between the patient's upper and lower anterior teeth. During the fabrication of dental restorations, a dentist must attempt to simulate as closely as possible the movement of the patient's mandible to both diagnose interferences between the patient's teeth and to check the fit of fabricated dental restorations prior to fitting the patient with the restorations.

An articulator is typically used to simulate the movement path of the patient's fossa and condyle pairs. Articulators commonly include upper and lower frame members connected together about at least a hinge axis for relative rotational movement. Thus, once casts of a patient's upper and lower teeth are attached to the upper and lower articulator frame members, respectively, two of the primary determinants of the patient's mandibular movement are recreated to help diagnose potential interferences between the patient's existing teeth and to aid in checking the fit of dental restorations.

Prior art articulators vary in complexity (and thus in the degree of accuracy with which they reproduce mandibular movement) from simple "hinge" articulators (typically used for partial restorations) to fully adjustable articulators (typically used for full mouth reconstructions). The simpler articulators are typically capable of little more than an opening about the hinge axis. Rotation of the lower frame member about the remaining two axes (the vertical and the sagittal) is either limited or prohibited, as is translational movement of the lower frame member. Thus, lateral excursions and protrusive movements of the mandible are not accurately simulated by these types of simple articulators. Semi-adjustable articulators allow for limited rotation and translation of the lower frame member relative to the upper frame member by mechanically recreating the human temporomandibular joints, typically through the use of spring biased hinges. Unfortunately, these mechanical temporomandibular joints do not accurately reproduce the complicated movements of the human condyles within the fossae of the maxilla. Indeed, many prior art articulators "invert" these functional elements, placing the condylar path simulating the fossa on the lower frame member and the condylar element simulating the condyle on the upper frame member, to simplify the operation of the articulator. Such an inversion further limits the accuracy of the articulator. Thus, a current need exists for a simple dental articulator which accurately reproduces a patient's mandibular movement.

It is with regard to this background information that the improvements available from the present invention have evolved.

SUMMARY OF THE INVENTION

One of the significant aspects of the dental articulator of the present invention is that it closely simulates the actual mandibular movement of a human jaw.

Another significant aspect of the present invention relates to the fact that the dental articulator may be quickly and easily mounted with dental casts.

A further significant aspect of the present invention relates to the fact that the dental articulator allows a broad range of movement so that mounted dental casts may be moved through excursions which may exceed even the largest natural excursions of a human jaw.

A still further significant aspect of the present invention relates to the fact that the dental articulator may be molded quickly and relatively inexpensively from plastic with a minimum number of movable parts.

These and other significant aspects and advantages are provided by the dental articulator of the present invention. The articulator preferably comprises two major components: an upper frame member and a lower frame member. The upper frame member includes an upper or maxillary mounting area for attachment of a maxillary dental cast. Reproductions of two human fossae are attached to the rear of the upper mounting area, each fossa defining a downwardly opening socket. The lower frame member includes a lower or mandibular mounting area for attachment of a mandibular dental cast. Reproductions of two human condyles extend upwardly from the rear of the lower mounting area. The condyles are adapted to fit within the sockets of the fossae and form a working joint which simulates the human temporomandibular joint. In the preferred embodiment of the articulator, an elastic band is placed around the upper and lower frame members to yieldingly maintain the upwardly extending condyles within the downturned sockets of the fossae. Thus, the preferred embodiment of the articulator utilizes only three components (upper and lower frame members and the elastic band) with no other moving parts to achieve its function of simulating human mandibular movement.

The accurate reproduction of the human temporomandibular joints allows the lower frame member (and the attached mandibular dental cast) to undergo protrusive and excursive movements similar to those of a human jaw. Indeed, a knowledgeable dentist or technician can manipulate the lower frame member through a variety of complex motions with a degree of accuracy that cannot be duplicated by simple mechanical hinges and joints as utilized in the prior art.

The preferred embodiment of the articulator includes attachments such as wires between each condyle and its associated fossa. The wires help to maintain the integrity of the temporomandibular joints and prevent the upper and lower frame members from becoming separated. The preferred embodiment further includes a groove formed in the upper and lower frame members to maintain the elastic band at a predetermined point relative to the fossae and condyles. Additionally, the preferred embodiment of the articulator includes a threaded incisal guidance pin and a correspondingly threaded pin holder attached to the upper frame member to allow for precise manipulation of the incisal guidance pin relative to the lower frame member.

A more complete appreciation of the present invention and its scope can be obtained from understanding the accompanying drawings, which are briefly summarized below, the following detailed description of a presently preferred embodiment of the invention, and the appended claims.

DETAILED DESCRIPTION OF THE PREFERRED EMBODIMENT

Figure 1:
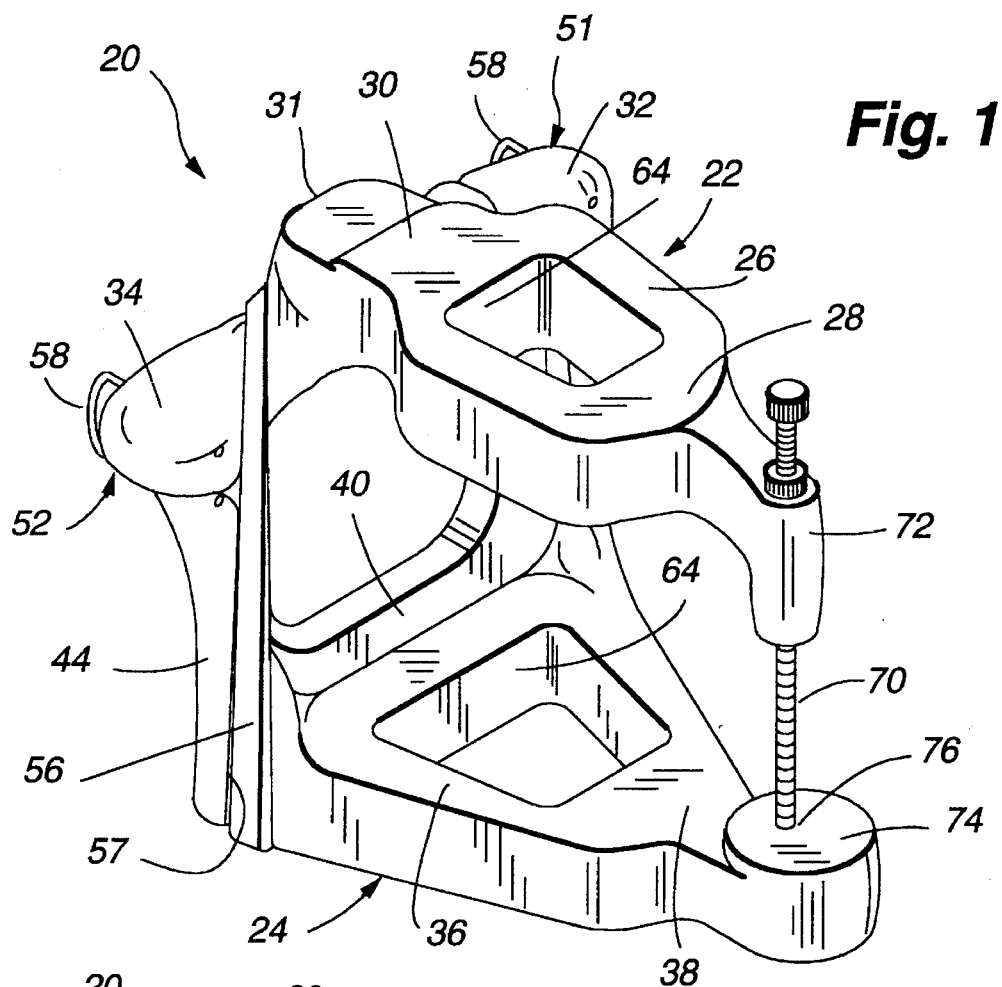
FIG. 1 is a perspective view of a dental articulator embodying the present invention.

FIG. 1 shows a preferred embodiment of a dental articulator 20 embodying the present invention. The articulator 20 includes an upper frame member 22 and a lower frame member 24 which are closely modeled after the maxilla and mandible, respectively, of a human jaw.

The upper frame member 22 includes a central maxillary mount 26 having an anterior end 28 and a posterior end 30. The posterior end 30 of the maxillary mount 26 is preferably integrated with a bridge 31 which connects reproductions of two human fossae. A left fossa 32 and a right fossa 34 (the left and right designations corresponding to those of a human jaw) are positioned at opposite ends of the bridge 31 to extend laterally outwardly and slightly downwardly from the maxillary mount 26 as shown in FIGS. 1, 2, 7 and 9. Each fossa 32 and 34 defines a downwardly opening socket 35 best shown in FIGS. 5–7.

The lower frame member 24 includes a central mandibular mount 36 having an anterior end 38 and a posterior end 40. Two opposing left and right side condylar members 42 and 44, respectively, are integrally formed with the posterior end 40 of the mandibular mount 36. The condylar members 42 and 44 rise upwardly and arch laterally outwardly and rearwardly from the mandibular mount 36 to preferably terminate in reproductions of two human condyles (a left condyle 46 and a right condyle 48), as shown in FIGS. 1–4 and 7. The left and right condyles 46 and 48 are shaped with a substantially flat anterior side 49 and a rounded posterior side 50 (best shown in FIGS. 5–7) to fit properly within the sockets 35 of the left and right fossae 32 and 34, respectively, and form left and right temporomandibular joints 51 and 52.

The upper and lower frame members 22 and 24 are preferably molded from a rigid plastic material in a conventional manner so that the fossae 32 and 34 and the condyles 46 and 48 correspond substantially to their counterparts in a human jaw. Although a rigid plastic material is used, the working elements of the articulator 20 are more flexible than those of prior art metal articulators. This added flexibility enhances the ability of the temporomandibular joints 51 and 52 to closely approximate the temporomandibular joints of a human jaw.

The accurate reproduction of the condyle-fossa relationship within the temporomandibular joints 51 and 52 allows the lower frame member 24 to be moved relative to the upper frame member 22 in a manner which corresponds closely to the movement of the human mandible relative to the maxilla. These movements include rotation of the lower frame member 24 about a hinge axis 53 (FIG. 7) through both condyles 46 and 48, a vertical axis 54 through one of the condyles 46 or 48 during a lateral excursion, and a horizontal sagittal axis 55 through the same condyle during the same lateral excursion. Additionally, the size of the temporomandibular joints 51 and 52 (as shown in FIGS. 5 and 6) and the flexible nature of the preferably plastic condylar members 42 and 44 allow a translational movement of the condyles 46 and 48 within their respective fossa 32 and 34 during a protrusive movement of the lower frame member 24.

Figure 2:
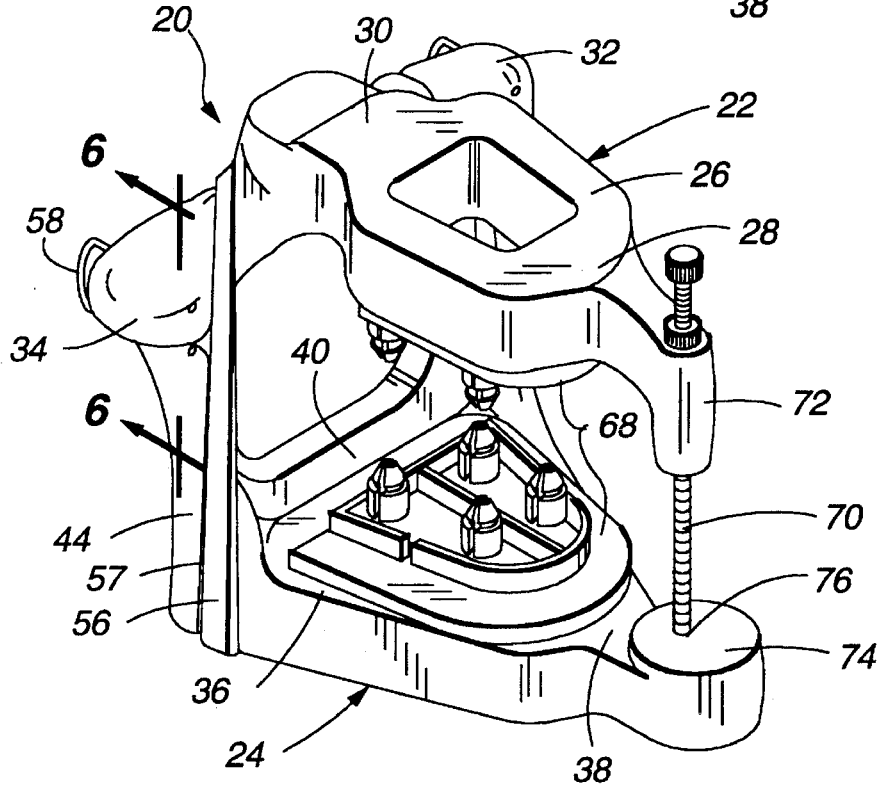
FIG. 2 is a perspective view illustrating the dental articulator of FIG. 1 with mounting plates attached to upper and lower frame members of the articulator.
Figure 7:
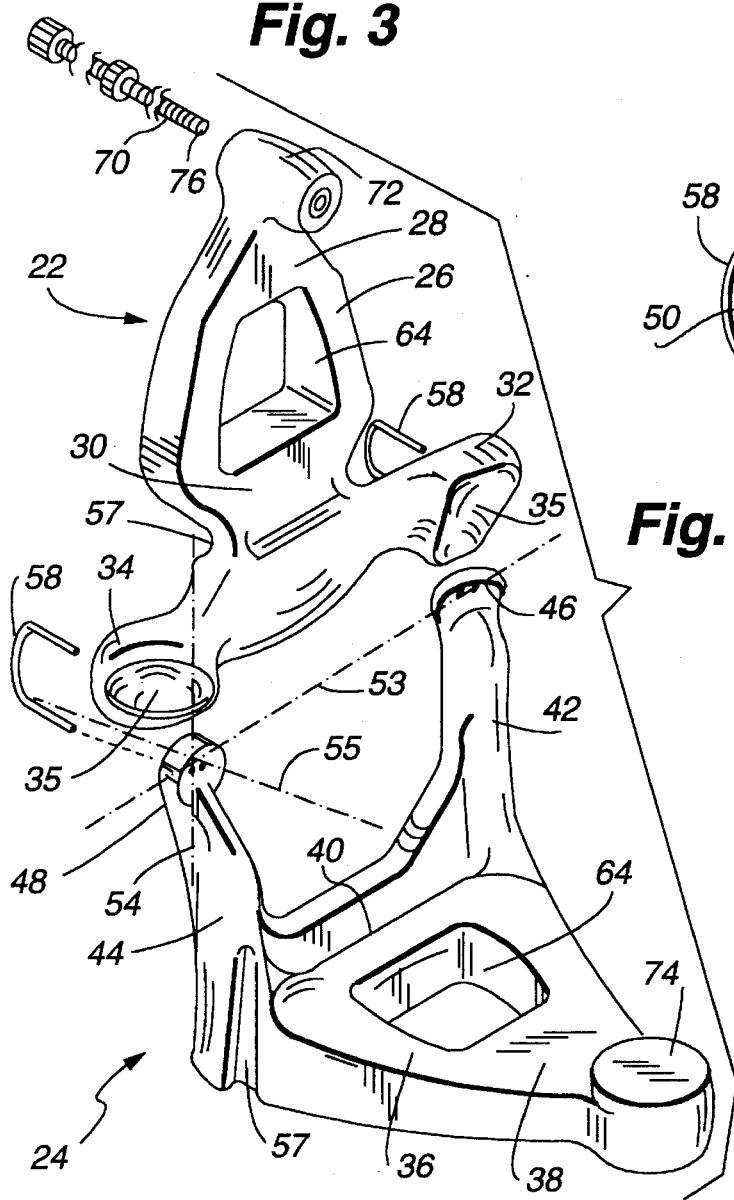
FIG. 7 is an exploded perspective view of the components of the dental articulator shown in FIG. 1.
Figure 8:
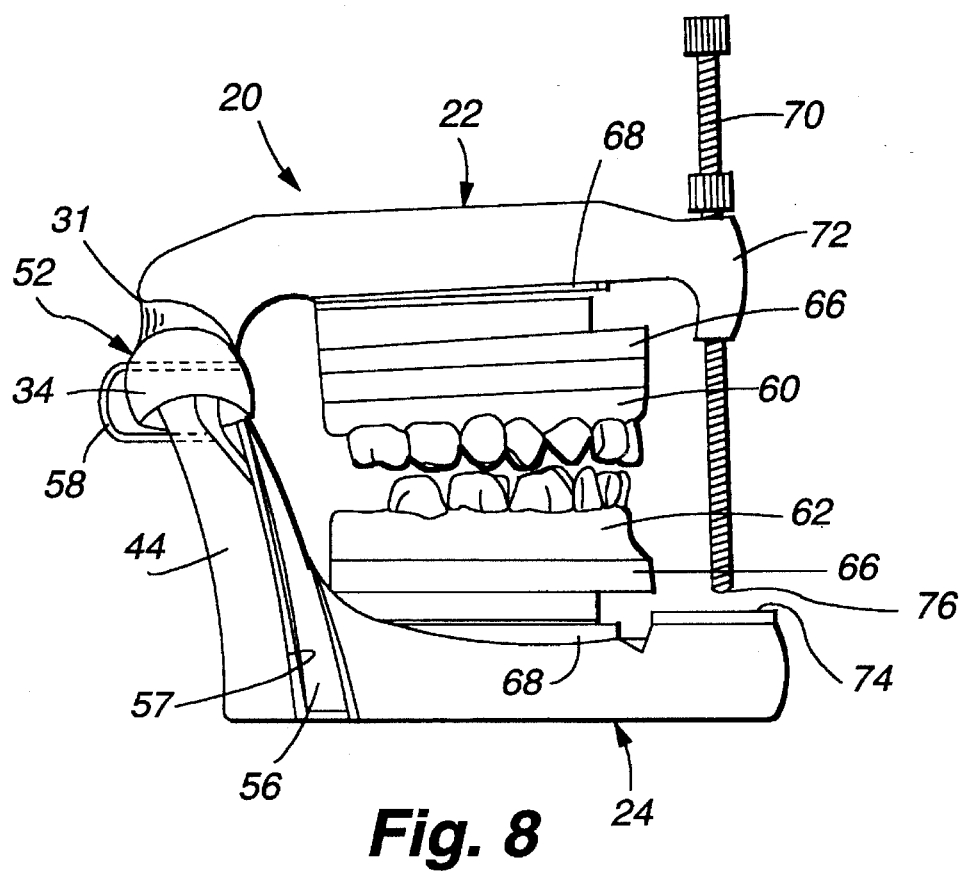
FIG. 8 is a left side elevation view illustrating the dental articulator of FIG. 2 with dental casts attached to the mounting plates on the upper and lower frame members of the articulator.
Figure 9:
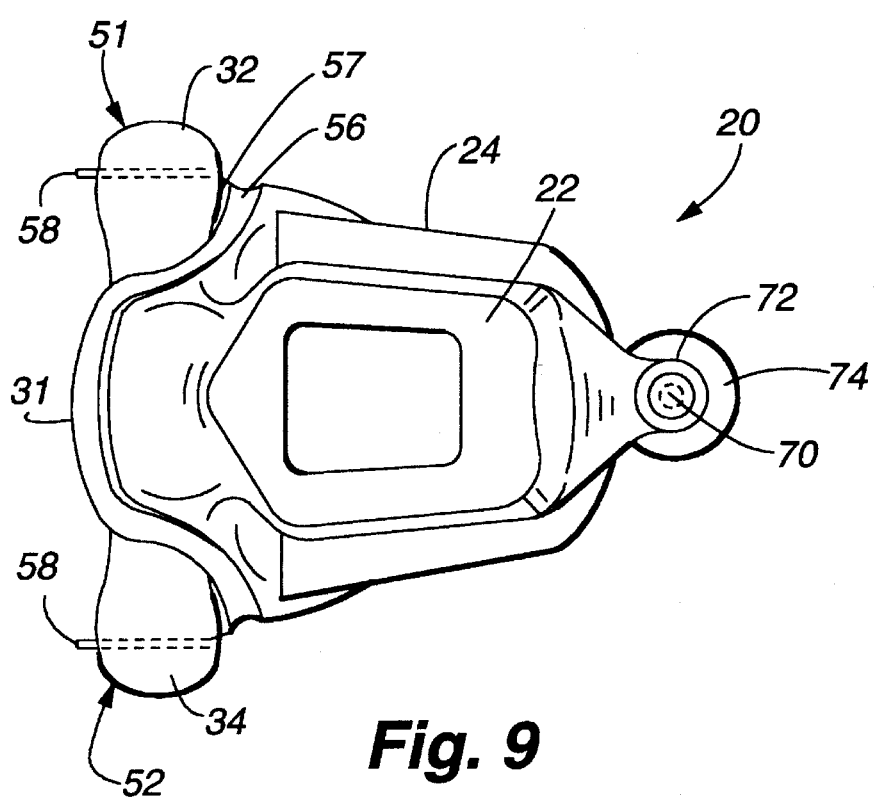
FIG. 9 is a top view of the dental articulator illustrated in FIG. 2.

A closed elastic band 56 is preferably wrapped around the posterior of the upper and lower frame members 22 and 24 as shown in FIGS. 1–4, 8 and 9. The elastic band 56 helps to yieldingly retain the condyles 46 and 48 seated within their respective fossae 32 and 34 during operation of the articulator 20. In its preferred position, the elastic band 56 passes between the temporomandibular joints 51 and 52 and the mounts 26 and 36 (FIGS. 1, 2 and 8). This preferred position of the elastic band 56 creates a slight torque about the horizontal hinge axis 53 so that the upper and lower frame members 22 and 24 tend to remain in a closed position relative to each other, as shown in FIGS. 1–4 and 8. Due to the proximity of the elastic band 56 to the hinge axis 53, the closing torque applied by the band is not so great as to hamper attempts to manipulate the frame members 22 and 24. A groove 57 for retaining the elastic band 56 is preferably formed in the upper and lower frame members 22 and 24 (FIGS. 1–4 and 7–9). The groove 57 maintains the elastic band 56 in its predetermined preferred position relative to the temporomandibular joints 51 and 52 and preferably has a width equal to the width of the elastic band 56 to prevent the elastic band from slipping out of the groove during operation of the articulator 20.

Figure 4:
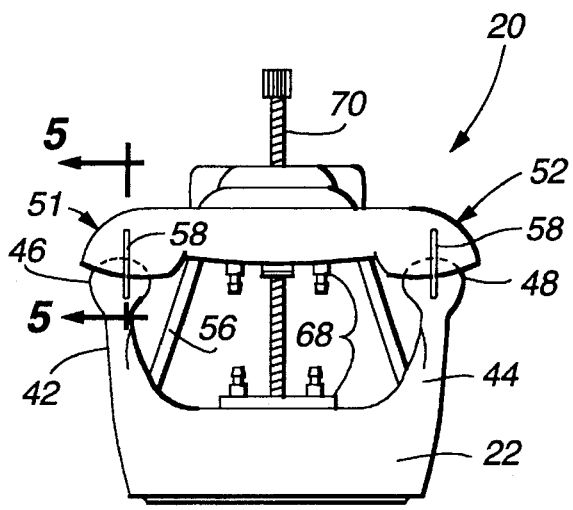
FIG. 4 is a rear elevation view of the dental articulator illustrated in FIG. 2.
Figure 5:
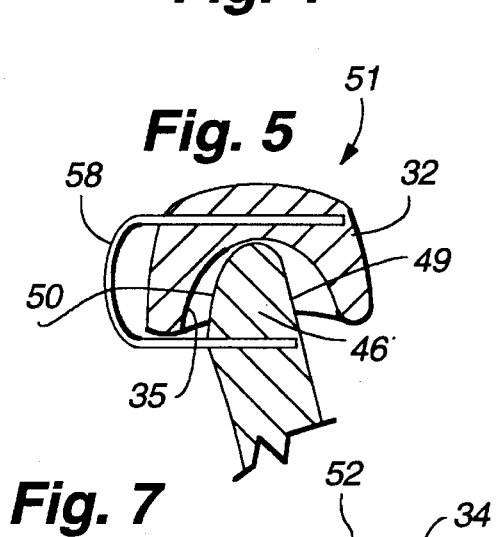
FIG. 5 is an enlarged partial section taken substantially in the plane of line 5—5 on FIG. 4.
Figure 6:
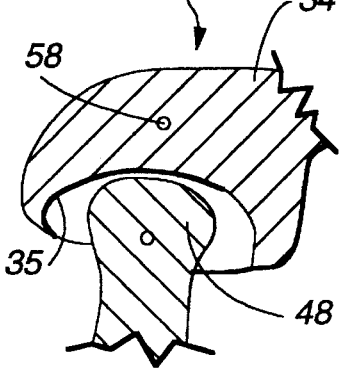
FIG. 6 is an enlarged partial section taken substantially in the plane of line 6—6 on FIG. 2.

The preferred embodiment of the articulator 20 may include attachments such as wires 58 running between each condyle 46 and 48 and its respective fossa 32 and 34 (FIGS. 4–6). The wires 58 may be made of any flexible material but are preferably plastic so that they may be more easily bonded to the preferably plastic material of the upper and lower frame members 22 and 24. The attachment of the fossae 32 and 34 to the condyles 46 and 48 helps to maintain the integrity of the temporomandibular joints 51 and 52 during operation of the articulator 20. Additionally, if the condyles should diverge from the fossae, the wires 58 would prevent the upper and lower frame members 22 and 24 from becoming completely separated (and potentially lost) from one another.

Dental casts may be attached to the upper and lower frame members 22 and 24 in a conventional manner. For example a maxillary cast 60 may be attached via a hot-melt adhesive bond to the maxillary mount 26, while a mandibular cast 62 may be attached in a similar manner to the mandibular mount 36. When using such an attachment process, the maxillary and mandibular mounts would preferably be formed substantially flat to provide an adequate surface for application of the adhesive. However, the preferred embodiment of the articulator 20 includes cutouts 64 in the maxillary and mandibular mounts 26 and 36, as shown in FIGS. 1 and 7. The cutouts allow the use of a conventional fast setting substance such as die-stone or plaster to attach the dental casts to the frame members. For example, once the maxillary cast 60 is properly positioned relative to the maxillary mount 26 in a known manner, a quick setting plaster compound could be poured into the cutout 64 atop the maxillary cast 60 and allowed to set within the cutout 64 until the cast 60 is bonded to the maxillary mount 26 of the upper frame member 22. The process could be repeated with the mandibular cast 62 by inverting the articulator, properly positioning the cast 62 relative to the mandibular mount 36 in a conventional manner and filling the cutout 64 as described above.

Figure 3:
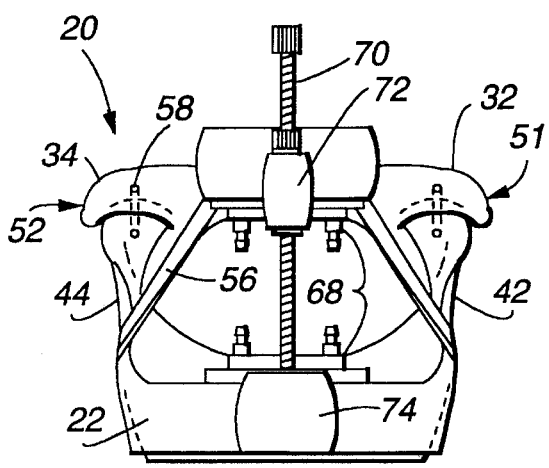
FIG. 3 is a front elevation view of the dental articulator illustrated in FIG. 2.

While the above described mounting process would effectively fix the dental casts to the upper and lower frame members, it would not permit the casts to be temporarily detached from the frame members during the formation of the dental restoration. Thus, the articulator 20 is preferably used with a separate system for mounting a dental cast to an articulator. Such a system is described in detail within U.S. patent application Ser. No. 08/085,812 (the "'812" Application) which is of common ownership with the present application, the disclosure of which is hereby incorporated by reference. The system of the '812 Application includes identical base plates 66 upon which the maxillary and mandibular dental casts 60 and 62 are mounted. The system further includes identical mounting plates 68 which are fixed to the maxillary and mandibular mounts 26 and 36. The mounting plates 68 are substantially flat on one side to enhance the preferably plaster bond with the upper and lower frame members (FIG. 2). A second side of the mounting plates 68 is adapted to releasably engage the base plates 66 as shown in FIGS. 2–4 and as described more fully in the '812 Application.

Once the maxillary and mandibular casts 60 and 62 are attached to their respective base plates 66, the base plates are attached to their respective mounting plates 68. The mounting plates are then fixed to the maxillary and mandibular mounts 26 and 36 as described above so that the maxillary and mandibular casts 60 and 62 are properly positioned on the upper and lower frame members 22 and 24, respectively. The base plates 66 and their attached casts 60 and 62 may then be easily removed from and reattached to the mounting plates 68 as required during the formation of the dental restorations while maintaining the proper alignment of the dental casts upon the articulator 20.

A preferred embodiment of the articulator 20 also includes an incisal guidance pin 70. The incisal guidance pin 70 is preferably threaded and adjustably retained within a correspondingly threaded pin holder 72. The pin holder 72 is attached to the anterior end 28 of the maxillary mount 26 as shown in FIGS. 1–3, 7 and 8, and is preferably formed integrally therewith during the molding of the upper frame member 22. Similarly, a table 74 is attached to the anterior end 38 of the mandibular mount 36 directly underneath the pin holder 72 when the upper and lower frame members 22 and 24 are in the closed position as shown in FIGS. 1–4 and 8. The incisal guidance pin 70 helps to determine the effect that a patient's anterior teeth have on his or her mandibular movement. The function and operation of the incisal guidance pin is well known in the art but will be summarized briefly in order to demonstrate the benefits of the threaded pin 70.

Once the maxillary and mandibular casts 60 and 62 are attached to the upper and lower frame members 22 and 24 and the articulator is closed as shown in FIG. 8, the incisal guidance pin 70 may be adjusted so that a lower end 76 of the pin 70 misses contacting the table 74 by approximately 1 millimeter in all excursions and protrusive movements of the lower frame member 24. The articulator 20 is then opened (i.e., the lower frame member 24 is rotated away from the upper frame member 22 about the hinge axis 53) and an uncured acrylic mixture (not shown) is built up on the table to a height of approximately 6–7 millimeters. Once the acrylic mixture has partially cured, the articulator 20 is closed so that the end 76 of the incisal guidance pin 70 penetrates the soft acrylic mixture. The lower frame member 24 is then moved through all the possible mandibular excursions and protrusive movements with the anterior teeth of the dental casts 60 and 62 in constant contact. In this manner, the end 76 of the incisal guidance pin 70 acts like a stylus forming a guide within the acrylic which can be used to duplicate the influence of the anterior teeth once the acrylic is fully cured.

Prior art incisal guidance pins are not threaded and are typically connected to the upper frame member by a set screw. This type of connection makes fine adjustments of the pin placement difficult when positioning the pin relative to the table 74. However, the threaded incisal guidance pin 70 and the correspondingly threaded pin holder 72 allow for minute changes in the position of the pin 70 relative to the table. Therefore, the operation of the incisal guidance pin 70 (and thus the accuracy of the articulator 20) is enhanced by utilizing a threaded pin and holder 72.

The articulator 20 of the present invention has several advantages over prior art articulators. First, in comparison to simple hinge articulators and semi-adjustable articulators, the articulator 20 more closely simulates the movement of the human mandible. The lower frame member 24 is able to rotate about three different axes and may be easily translated to simulate protrusive movements of the mandible. These movements are enhanced by the flexible nature of the working elements (the condyles, fossae and the condylar members) in the preferred plastic embodiment of the articulator 20. Additionally, the articulator 20 utilizes only three major components (upper and lower frame members 22 and 24 and the elastic band 56) so that the articulator is simple to use and relatively inexpensive to manufacture. The elastic band 56 both yieldingly retains the condyles 46 and 48 within the sockets 35 of the fossae 32 and 34 and applies a slight closing torque to the articulator when the band is preferably positioned as described above. However, the condyles may be easily removed from the fossae should the dentist so desire (e.g., when simulating mandibular excursions beyond the normal masticatory scheme such as when checking for interferences). Furthermore, although the articulator 20 will operate well with any type of dental casts, it is designed specifically to operate with a system for releasably mounting dental casts such as that shown in the '812 Application. Lastly, the articulator 20 utilizes a threaded incisal guidance pin 70 and pin holder 72 for enhanced positioning of the pin 70 relative to the table 74.

A presently preferred embodiment of the present invention and many of its improvements have been described with a degree of particularity. This description has been made by way of preferred example and is based on a present understanding of knowledge available regarding the invention. It should be understood, however, that the scope of the present invention is defined by the following claims, and not necessarily by the detailed description of the preferred embodiment.

The invention claimed is:

1. A dental articulator comprising:

an upper frame member having an upper mounting area adapted to be attached to a maxillary dental cast and including two opposing fossae extending laterally outwardly from a posterior end of said upper mounting area, each fossa defining a downwardly opening socket;

a lower frame member having a lower mounting area adapted to be attached to a mandibular dental cast and including two opposing condyles extending upwardly from a posterior end of said lower mounting area, said opposing condyles adapted to fit within said sockets of said opposing fossae to substantially duplicate opposing temporomandibular joints of a human jaw; and an elastic band surrounding said upper and lower frame members to yieldingly maintain said condyles within said sockets.

2. An articulator as defined in claim 1, wherein said upper and lower frame members are substantially molded from a rigid plastic material.

3. An articulator as defined in claim 1, wherein said elastic band is arranged on said upper and lower frame members at a predetermined postion between said temporomandibular joints and said mounting areas.

4. An articulator as defined in claim 3, wherein said upper and lower frame members further include a groove adapted to retain said elastic band at said predetermined position.

5. An articulator as defined in claim 1, further comprising a wire attached between each said condyle and its associated fossa.

6. An articulator as defined in claim 1, wherein each said fossa is formed integrally with said upper frame member and each said condyle is formed integrally with said lower frame member.

7. An articulator as defined in claim 6, further comprising two opposing condylar members formed integrally with said lower frame member and extending upward from said posterior end of said lower mounting area, said condylar members terminating in said condyles.

8. An articulator as defined in claim 1, wherein:

said upper frame member further includes an incisal guidance pin holder attached to an anterior end of said upper mounting area; and said lower frame member further includes an incisal guidance pin table attached to an anterior end of said lower mounting area, said table positioned substantially beneath said pin holder when said upper and lower frame members are in a closed position relative to one another.

9. An articulator as defined in claim 8 wherein said incisal guidance pin holder is threaded, said articulator further comprising:

a threaded incisal guidance pin adapted to engage said threaded incisal guidance pin holder for vertical movement relative to said incisal guidance pin table.

10. A dental articulator comprising:

an upper frame member having an upper mounting area adapted to be attached to a maxillary dental cast and including two opposing fossae formed integrally with a posterior end of said upper mounting area, said fossae extending laterally outwardly from said upper mounting area, and each fossa defining a downwardly opening socket;

a lower frame member having a lower mounting area adapted to be attached to a mandibular dental cast and including two opposing condylar members formed integrally with a posterior end of said lower mounting area, said condylar members extending upwardly from said lower mounting area;

said two opposing condylar members terminating in two opposing condyles adapted to fit within said opposing fossae to substantially duplicate opposing temporomandibular joints of a human jaw; and an elastic band surrounding said upper and lower frame members to yieldingly maintain said condyles within said fossae.

11. An articulator as defined in claim 10, wherein said upper and lower frame members are substantially molded from a rigid plastic material.

12. An articulator as defined in claim 10, wherein said elastic band is arranged on said upper and lower frame members at a predetermined postion between said fossa and condyle pairs and said mounting areas.

13. An articulator as defined in claim 12, wherein said upper and lower frame members further include a groove adapted to retain said elastic band at said predetermined position.

14. An articulator as defined in claim 10, wherein:

said upper frame member further includes a threaded incisal guidance pin holder attached to an anterior end of said upper mounting area;

said lower frame member further includes an incisal guidance pin table attached to an anterior end of said lower mounting area, said table positioned substantially beneath said pin holder when said upper and lower frame members are in a closed position relative to one another, and further comprising:

a threaded incisal guidance pin adapted to engage said threaded incisal guidance pin holder for vertical movement relative to said incisal guidance pin table.

15. An articulator as defined in claim 10, further comprising a wire attached between each said condyle and its associated fossa.

* * * * *